United States Patent [19]

Bunning

[11] Patent Number: 5,001,274
[45] Date of Patent: Mar. 19, 1991

[54] HYDROFORMYLATION PROCESS

[75] Inventor: Donald L. Bunning, South Charleston, W. Va.

[73] Assignee: Union Carbide Chemicals And Plastics Company Inc., Danbury, Conn.

[21] Appl. No.: 370,806

[22] Filed: Jun. 23, 1989

[51] Int. Cl.$^5$ .............................................. C07C 45/50
[52] U.S. Cl. ................................... 568/454; 568/451; 568/492
[58] Field of Search ................ 568/451, 454, 492, 449

[56] References Cited

U.S. PATENT DOCUMENTS

| | | | |
|---|---|---|---|
| 2,748,167 | 5/1956 | Hagemeyer et al. | 260/604 |
| 3,455,091 | 7/1969 | Herber et al. | 55/84 |
| 3,527,809 | 9/1970 | Pruett et al. | 260/604 |
| 4,148,830 | 4/1979 | Pruett et al. | 260/604 |
| 4,210,426 | 7/1980 | Sridhar | 55/68 |
| 4,247,486 | 1/1981 | Brewester et al. | 568/454 |
| 4,260,828 | 4/1981 | Morrell et al. | 568/454 |
| 4,277,627 | 7/1981 | Bryant et al. | 568/454 |
| 4,283,562 | 8/1981 | Billig et al. | 568/454 |
| 4,297,239 | 10/1981 | Bryant et al. | 252/412 |
| 4,374,278 | 2/1983 | Bryant et al. | 568/454 |
| 4,440,548 | 4/1984 | Hill | 55/26 |
| 4,482,749 | 11/1984 | Dennis et al. | 568/454 |
| 4,491,675 | 1/1985 | Abatjoglou et al. | 568/454 |
| 4,533,755 | 8/1985 | Cornils et al. | 568/454 |
| 4,577,043 | 3/1986 | Kalbfell et al. | 568/454 |
| 4,593,127 | 6/1986 | Bunning et al. | 568/454 |
| 4,599,206 | 7/1986 | Billig et al. | 558/85 |
| 4,613,701 | 9/1986 | Strong | 568/454 |
| 4,668,651 | 5/1987 | Billig et al. | 502/158 |
| 4,737,588 | 4/1988 | Billig et al. | 556/12 |
| 4,792,636 | 12/1988 | Hensman et al. | 568/454 |
| 4,871,879 | 10/1989 | Laird | 568/454 |

FOREIGN PATENT DOCUMENTS

| | | | |
|---|---|---|---|
| 0157755 | 10/1985 | European Pat. Off. | 568/492 |
| 3301591 | 7/1984 | Fed. Rep. of Germany | 568/454 |
| WO8001690 | 8/1980 | PCT Int'l Appl. | |

*Primary Examiner*—Werren B. Lone
*Attorney, Agent, or Firm*—Reynold J. Finnegan

[57] ABSTRACT

An improved process for the rhodium-catalyzed hydroformylation of olefins to aldehydes is described. The improvement provides a means for recovering valuable components in gaseous streams by scrubbing the streams with a stripped or cooled catalyst solution.

17 Claims, 1 Drawing Sheet

HYDROFORMYLATION PROCESS

BACKGROUND OF THE INVENTION

1. Field of the Invention

This invention relates to a process for the production of aldehydes by the rhodium-catalyzed hydroformylation of olefins; and particularly to an improvement in such a process wherein unreacted olefin and product aldehydes are recovered from internal and vent gaseous streams by absorption with catalyst solution.

2. Background of the Invention

Processes for forming oxygenated products such as aldehydes by hydroformylation of an olefin with carbon monoxide and hydrogen are well known in the art. The aldehydes produced correspond to compounds obtained by the addition of a carbonyl group to an olefinically unsaturated carbon atom in the starting material with simultaneous saturation of the olefinic bond. Such processes are generally known in the industry by various names such as hydroformylation or oxo processes, reactions, or syntheses and/or oxonation.

Early prior art hydroformylation processes employed cobalt octacarbonyl catalysts. Disadvantages of such processes included the requirement for high operative pressure and an inability to obtain products with an high normal to branched-chain isomer ratio.

A significant improvement in oxo process technology was disclosed by R.L. Pruett and J.A. Smith in U.S. Pat. No. 3,527,809. Pruett & Smith's process is characterized by a high normal to branched-chain aldehyde isomer ratio obtained at a high yield and at low temperatures and pressures by contacting an alphaolefin with certain rhodium complex catalysts in the presence of hydrogen and carbon monoxide under a defined set of variables. The variables included (1) the rhodium complex catalyst, (2) the olefin feed, (3) a triorganophosphorus ligand and its concentration, (4) a relatively low temperature, (5) relatively low total hydrogen and carbon monoxide pressure and (6) the partial pressure exerted by carbon monoxide.

Further improvements have been made over the years with regard to, e.g., the hydroformylation reaction solvent (see U.S. Pat. No. 4,148,830); the use of a gas recycle stream to control the liquid body in the hydroformylation reactor (see U.S. Pat. No. 4,247,486); controlling the hydroformylation reaction conditions to minimize rhodium complex catalyst deactivation (see U.S. Pat. No. 4,277,627); the use of alkyldiarylphosphines to improve the stability of the rhodium complex catalyst (see U.S. Pat. No. 4,260,828); the reactivation of deactivated rhodium complex catalysts by concentration and optional oxygen and/or base treatments (see U.S. Pat. Nos. 4,297,239 and 4,374,278) and the use of reactors in series (see U.S. Pat. No. 4,593,127).

Regardless of whether a liquid or gas recycle process is employed, gaseous purges or vent streams exist. These streams are in some cases necessary to allow inerts and excess hydrogen to escape from the system while in other cases they arise merely as a consequence of certain processing steps and are not really necessary to the overall operation of the system. Because the content of these purges resembles product streams, it is possible to apply conventional recovery technology in an attempt to enhance overall process efficiency. However, often these purges are allowed to escape primarily because their value does not justify the cost of installing and operating compressors, chillers, or other complicated recovery equipment even though they contain significant quantities of unreacted olefin, product aldehydes and alcohols.

The use of techniques, often referred to in the art as "scrubbing" techniques, to recover components from mixed gas streams is well known. Generally, a gas stream is contacted with a suitable liquid solvent in a countercurrent fashion, and portions of the gas are selectively absorbed into the liquid solvent. The resulting liquid solution is normally taken to another piece of equipment where the dissolved gases are separated (i.e., desorbed) from the liquid solvent. Various techniques may be employed to accomplish this separation, with distillation being a common example. The solvent may then be recycled to the gas-liquid contactor.

In general, such a scrubbing operation involves at least two major pieces of equipment the primary gas-liquid contactor and the equipment to separate the dissolved gas from the liquid. In addition, various pieces of minor equipment are also involved: pumps, condensers, heat exchangers, systems for making up for solvent losses, storage tanks for the solvent, etc. Often other major equipment is also required to separate and recover the various components of the desorbed gas stream. It is generally appreciated that significant energy costs are associated with the employment of this equipment.

The operation of such a scrubbing system with a typical organic liquid solvent can be rather complicated, and expensive. In addition, it introduces a foreign material—the solvent—which will tend to contaminate the recovered gas and infiltrate the basic process if the recovered gases are recycled. In the case of rhodium-catalyzed hydroformylation processes, even rather minor contamination of the rhodium-complex catalyst by such solvents can have serious consequences.

The prior art describes various techniques to recover components from oxo-process vent streams. For example, West German Offenlegungsschrift 3102281A1 relates to a method for recovery of unreacted raw materials in the off-gas from a high pressure oxo process. Specifically, the method relates to the hydroformylation of propylene by simultaneously operating a high pressure oxo reactor employing a cobalt-based catalyst and a low pressure oxo reactor employing a rhodium-based catalyst, characterized by the introduction of waste gas resulting from catalyst recovery from the high pressure reaction, which still contains considerable amounts of unconverted propylene, carbon monoxide and hydrogen, into the low pressure reactor. An alternative approach was taken in U.S. Pat. No. 4,533,755 wherein the off-gas from a lower pressure rhodium-catalyst system is compressed and converted in a high pressure cobalt-catalyst system. These disclosures illustrate the complexity and expense of methods which address the recovery of unreacted materials from vent streams. U.S. Pat. No. 3,455,091 discloses a process for separating product aldehydes (particularly n-butyraldehyde and iso-butyraldehyde) from the off-gas formed in an oxo process (i.e., reaction of an appropriate olefin with hydrogen and carbon monoxide in the presence of cobalt carbonyl) by scrubbing the off-gas with a solvent which comprises a high boiling point oxonation product or a high boiling point hydrogenated oxonation product. The off-gas is said to consist essentially of the product aldehydes and carbon monoxide and hydrogen together with small amounts of saturated and unsaturated hydrocarbons having two to four carbon atoms and small amounts of inert gas, such as nitrogen. The aldehyde content of the off-gas varies depending upon the composition of the oxonation product and on the temperature and pressure at which flashing is carried out. The scrubbing solvent used is a high-boiling oxonation product having a boiling point of advantageously more than 95° C., preferably more than 150° C. The preferred solvents, consisting essentially of higher aldehydes formed by aldol condensation of lower aldehydes, acetals, carboxylic esters and higher alcohols, may be obtained as the distillation residue of the processing of the oxo reaction mixture. However, it is also disclosed in U.S. Pat. 4,455,091 at column 2, lines 39-41 that the -main product of the oxo reaction is also suitable provided its boiling point is above 95° C., for example, butanol or n-propanol.

It is further disclosed that the scrubbing solvent containing the aldehydes may be processed together with the bulk of the product obtained in the oxo reaction. During the scrubbing of the off-gas, the solvent is advantageously at room temperature, for example at 15° C. to 25° C., with particularly good results obtained when the solvent is kept at 5° C. to 10° C. Scrubbing of the off-gas is in general carried out at pressures of 0 to 30 atmospheres gauge.

U.S. Pat. No. 2,748,167 discloses a process for preparing oxygenated products such as butyraldehyde by the reaction of an olefin (e.g. propylene), carbon monoxide and hydrogen in the presence of a cobalt catalyst. The patent provides for the escape from the reactor to a condenser of unreacted process gas and vaporized product materials such as normal- and isobutyraldehydes and other products, as well as butanol. The resulting gas and condensate mixture is then passed to a liquid-gas separator to separate the liquid portion from the process gas (primarily unreacted carbon monoxide and hydrogen) which is reintroduced to the reactor. The patent teaches the removal of vent gas from the system in order to reduce the build-up of inerts in the reactor space, thus maintaining the desired synthesis gas composition. The vent gas may also be fed to an alcohol scrubber to recover the olefin portion of the gas.

The liquid removed from the liquid-gas separator, containing crude product and dissolved olefin, is passed to a pressure distillation column to separate and recover olefin for return to the reaction. The crude product may be subjected to subsequent operations, such as distillations, to obtain the various aldehydes in purified form.

U.S. Pat. No. 4,210,426 discloses that when propene (i.e. propylene) is subjected to hydroformylation, gas mixtures are obtained in addition to liquid reaction products such as n-butyraldehyde, iso-butyraldehyde, n-butanol and iso-butanol. These gas mixtures are said to consist of the unconverted components (carbon monoxide, hydrogen and propene) and of propane. It is disclosed that they had been previously burned as off-gases or converted, together with by-product isobutyraldehyde, to the reactants necessary for the hydroformylation, but that such conversion is no longer economical. It is also disclosed that propene and propane may be recovered from these gas mixtures by condensation, by extractive distillation or by absorption using a recovery agent. However, the patent discloses that these processes are unsuitable and uneconomic because they are eithher expensive or have the considerable disadvantage that the recovered gases require careful purification before being reemployed in the hydroformylation.

The invention described in the U.S. Pat. No. 4,210,426 is the use of the liquid hydroformylation products to absorb propene and propane from the off-gases. It is said that these absorbents offer the great advantage that, after desorption, small amounts of the absorbents do not have to be separated off but can be recycled to the hydroformylation reaction together with recovered propane. The preferred absorbents include iso- or n-butyraldehyde, although iso-butyraldehyde is particularly used since it is more stable to heat and also since n-butyraldehyde is the valuable main product of the hydroformylation.

High pressures (i.e., 10 to 60 bars) and low temperatures (i.e., 0-50° C., preferably 20-40° C.) are said to increase the absorption effect it possible to obtain a gas product, largely free of propene and propane, essentially consisting of carbon monoxide and hydrogen which can be recycled to the hydroformylation reaction. The absorbed propene and propane is desorbed (i.e., separated from the absorbent) in a known manner; for example, propene only may be separated first by combining the desorption with a fractional distillation, leaving propane in the absorbent and preferably recycling the separated propene to the hydroformylation reaction. Subsequently, the remaining propane in the absorbent may be separated by distillation and the absorbent recycled to the hydroformylation.

Although U.S. Pat. No. 4,210,426 employs hydroformylation products as a scrubbing solvent and thereby avoids contamination of the catalyst solution, it teaches a standard scrubbing arrangement to recover the propylene and propane from the reactor vents by desorption from the scrubbing solvent. As with typical scrubbing arrangements, and in direct contrast to the present invention, a desorption step is used in the process disclosed by U.S. Pat. No. 4,210,426.

SUMMARY OF THE INVENTION

The present invention provides a process for recovering absorbable components such as unreacted olefin and product aldehyde, from gaseous streams vented from, or otherwise existing in, a hydroformylation reaction system, by contacting such gaseous streams with the hydroformylation catalyst solution to absorb such components therein. The resulting catalyst solution is then returned directly to the hydroformylation reaction; no desorption or separation is required or contemplated.

BRIEF DESCRIPTION OF THE DRAWINGS

The drawings schematically illustrate two embodiments of the process of this invention incorporated into a liquid recycle hydroformylation process. FIG. 1A illustrates an embodiment of the invention in which a single scrubber is employed, while

DETAILED DESCRIPTION OF THE INVENTION

This invention provides a simple and inexpensive way to recover unreacted olefin, product aldehyde, and other soluble components from gaseous vent streams from a hydroformylation reaction system, or other gaseous streams existing in the system, by scrubbing the gaseous streams with stripped or cooled hydroformylation catalyst solution. It avoids much of the normal expense and difficulty associated with standard solvent scrubbing systems. A major advantage of this invention is that it completely eliminates the need to separate the dissolved gases from the scrubbing solvent, because the catalyst solution in the scrubber tails can be returned directly to the reactor. Not only does this invention eliminate the need for a desorption step, it also eliminates the need to separate and/or process the recovered gases since the scrubber tails containing the dissolved gases are returned directly to the reactor, thereby significantly reducing the energy requirement of the process. In a typical application, only a simple packed column and a pump are required; however, some applications may justify a more sophisticated design. This invention also eliminates concerns about process contamination with a foreign scrubbing solvent. Furthermore, this scheme is readily adaptable to low pressure oxo processes because generally, a stripped or cooled catalyst stream already exists.

This invention is useful to selectively separate soluble components from internal streams which are not vented from the hydroformylation process. For example, in series reaction systems where a gas stream flows from one reactor to the next, it is often desirable to minimize olefin transfer from an upstream reactor to a downstream reactor. The present invention can be utilized to separate olefin (and other soluble components) from the lighter gases so that olefin can be returned to the upstream reactor(s). Returning olefin to the upstream reactor increases overall process efficiency by minimizing the amount of olefin that is allowed to pass through the reaction steps unreacted. Furthermore, the liquid that flows from one reactor to the next in a series reactor scheme may be flashed to remove as a gas a portion of the olefin dissolved therein and olefin may be recovered from the resulting gas by the technique of the present invention.

Although the present invention is useful in conjunction with any hydroformylation process, it is particularly useful when combined with a rhodium-catalyzed, low pressure hydroformylation process of the type first disclosed in the aforementioned U.S. Pat. No. 3,527,809, the disclosure of which is incorporated herein by reference. The present invention may also be combined with any of the rhodium-catalyzed hydroformylation processes disclosed in any of the following other aforementioned U.S. Pat. Nos. 4,148,830; 4,247,486; 4,260,828; 4,277,627; 4,297,239; 4,374,278; and 4,593,127; the disclosures of which are also incorporated herein by reference.

Since the present invention is concerned primarily with recovering olefin and/or aldehyde from vent streams or other existing gas streams in a hydroformylation process, it is not limited to any particular hydroformylation process or set of hydroformylation conditions. However, so that those skilled in the art can understand and practice the present invention and for purposes of illustration only, the present invention will be described hereinbelow in conjunction with a rhodium-catalyzed, low pressure hydroformylation process of the type described in the patents identified in the immediately preceding paragraph. It is to be understood, however, that it is not the intention to otherwise limit the practice of the present invention to such processes.

The improved hydroformylation process in which the present invention is particularly useful comprises contacting an olefin with carbon monoxide and hydrogen in the presence of a rhodium catalyst, and preferably also in the presence of a solvent and free (i.e., uncomplexed) triorganophosphorus ligand, at a temperature of from about 50° C. to about 140° C., to yield an aldehyde having one carbon atom more than the olefin. The rhodium catalyst may be any non-volatile rhodium catalyst that is effective for hydroformylation of the particular olefin employed; however, the preferred catalyst is a rhodium complex catalyst which consists essentially of rhodium in complex combination with carbon monoxide and an organophosphorus ligand (which may be an organophosphine compound and may be the same as, or different from, the free organophosphorus ligand). Each organo group of these tertiary phosphorus compounds is preferably a hydrocarbon group and may be the same or different as the other organo groups. The organo groups are preferably nonionic. In addition to a triorganophosphine, the organophosphorus ligand may also be, for example, a diorganophosphite, a bisphosphite or a diphosmonoxide as described in U.S. Pat. Nos. 4,599,206, 4,668,651 and 4,737,588.

Illustrative rhodium - triorganophosphine complex catalysts include those disclosed in the aforementioned U.S. Pat. Nos. 3,527,809; 4,148,830; 4,247,486; and 4,260,828; and also in the following patents and published patent applications, the disclosures of which are incorporated herein by reference: U.S. Pat. No. 4,283,562; 4,440,548; 4,482,749; 4,491,675; and 4,593,127; and PCT Application, Publication No. WO 80/01690 (published August, 1980). Of course, mixtures of different catalysts and organophosphine ligands can be employed if desired. Moreover, as noted in said references, the hydroformylation processes are generally and preferably carried out in the presence of free triorganophosphine ligand, i.e., ligand that is not complexed with the rhodium complex catalyst employed. While it is generally preferred that the free ligand be the same as the triorganophosphine ligand complexed with the rhodium, such is not necessary. Accordingly, it is to be understood that in the case of the rhodium - triorganophosphine complex catalyst, as well as in the case of the free triorganophosphine ligand, any conventional triorganophosphine ligand, heretofore suggested for use in such hydroformylation processes, such as disclosed e.g., by the above mentioned references, can be employed herein.

Accordingly, illustrative triorganophosphines that may be employed, either as the free ligand and/or as the complexed ligand of the rhodium complex catalyst, include, e.g., triarylphosphines, trialkylphosphines, alkyldiarylphosphines, dialkylarylphosphines, dicycloalkylarylphosphines, cycloalkyldiarylphosphines, triaralkylphosphines, tricycloalkylphosphines, and trialkylphosphines, alkyl and/or aryl bisphosphines and bisphosphine mono-oxides, and the like. Of course any of the hydrocarbon radicals of such triorganophosphines may be substituted if desired, with any suitable substituent that does not unduly adversely affect the desired result of the hydroformylation process or this invention. Illustrative substituents are corresponding hydrocarbon radicals such as alkyl, aryl, aralkyl, alkaryl and cyclohexyl substitutents, as well as other substituents which include, for example, silyl radicals such as $-Si(R^9)_3$; amino radicals such as $-N(R^9)_2$; acyl radicals such as $-C(O)R^9$; acyloxy radicals such as $-OC(O)R^9$; amido radicals such as $-CON(R^9)_2$ and $-N(R^9l)COR^9$; sulfonyl radicals such as $-SO_2R^9$; alkoxy radicals such as $-OR^9$; thionyl radicals such as —$SR^9$; phosphonyl radicals such as —$P(O)(R^9)_2$; as well as, halogen, nitro, cyano, trifluoromethyl, hydroxy radicals, and the like, wherein each $R^9$ individually represents the same or different monovalent hydrocarbon radical having from 1 to 18 carbon atoms (e.g., alkyl, aryl, aralkyl, alkaryl and cycloalkyl radicals); with the proviso that in amino substituents such as —$N(R^9)_2$, each $R^9$ taken together can also represent a divalent bridging group that forms a heterocyclic radical with the nitrogen atom; and with the further proviso that in amido substituents such as —$CON(R^9)_2$ and —$N(R^9)COR^9$, each $R^9$ also bonded to N can also be hydrogen. Of course it is to be understood that any of the substituted or unsubstituted hydrocarbon radicals that make up a particular triorganophosphine may be the same or different.

Such triorganophosphines and corresponding rhodium-triorganophosphine complex catalysts and methods for their preparation are well known (see, e.g., the above-mentioned references). Preferred triorganophosphines are those having the formula $(R^{10})_3P$ wherein each $R^{10}$ individually represents a monovalent hydrocarbon radical containing from 1 to 18 carbon atoms selected from alkyl, aralkyl, alkaryl, cycloalkyl and aryl radicals, as disclosed, e.g., in U.S. Pat. Nos. 3,527,809 and 4,283,562, and Among the more preferred triorganophosphines are triphenylphosphine, propyldiphenylphosphine, tert-butyldiphenylphosphine, n-butyldiphenylphosphine, n-hexyldiphenylphosphine, cyclohexyldiphenylphosphine, dicyclohexylphenylphosphine, tricyclohexylphosphine, trinaphthylphosphine, tritolylphosphine, tri(p-biphenyl)phosphine, tri(p-methoxyphenyl) phosphine, tri(m-chlorophenyl) phosphine, p-N,N-dimethylamino-phenyl bis-phenyl phosphine, and the like. While the choice of phosphorus ligand will depend upon factors such as the particular olefin being hydroformylated, the most preferred ligand (for use with the olefin, propylene) is triphenylphosphine ("TPP"), while the most preferred catalyst is a rhodium-TPP complex.

The catalyst terminology "consisting essentially of" is not meant to exclude, but rather to include, the presence of any other ligand which is complexed with the rhodium and which does not unduly adversely affect the hydroformylaton process. For example, in addition to carbon monoxide and triorganophosphine, hydrogen may also be complexed with the rhodium as a ligand. In this case, the hydrogen is derived from the hydrogen gas fed to the hydroformylation reaction, if not already present in the catalyst precursor.

The hydroformylation catalyst may be formed in situ during the hydroformylation reaction or a preformed rhodium hydrodocarbonyl-tris(triorganophosphine) such as the stable crystalline solid, rhodium hydrocarbonyl-tris (triphenylphosphine), $RhH(CO)(PPh_3)_3$, may be introduced into the reaction medium of the hydroformylation reactions. Alternatively rhodium catalyst precursors such as $Rh_2O_3$, $Rh_4(CO)_{12}$, $Rh_6(CO)_{16}$, $Rh(NO_3)_3$ or rhodium dicarbonyl acetylacetonate, and the like, may be introduced into the reaction medium of the hydroformylation reaction. In any event, an active rhodium complex hydroformylaton catalyst is present in the hydroformylation reaction medium- under the conditions of hydroformylations.

Rhodium concentrations in the range of from about 5 to about 10,000 ppm, and more preferably from about 10 to about 1000 ppm, of rhodium, calculated as rhodium metal, should be sufficient for most hydroformylation processes.

As noted above the triorganophosphine ligands defined herein are preferably employed in this invention as both the ligand complexed with rhodium as well as the free ligand also present. The amount of free ligand is at least one mole of ligand per mole of rhodium metal present in the liquid starting material. In general, an amount of free ligand of from about 2 to about 300, preferably from about 5 to about 200, moles per mole of rhodium metal present in the reaction medium, should be suitable for most hydroformylation reactions.

A hydroformylation reaction temperature in the range of from about 60° C. to about 130° C. is preferred and it will usually be convenient to operate at a temperature of from about 85° C. to about 125° C.

The total gas pressure of hydrogen, carbon monoxide and olefin may range from about 1 to about 10,000 psia, although it is preferred that the hydroformylation process be operated at a total gas pressure of hydrogen, carbon monoxide and olefin of less than about 1500 psia and more preferably less than about 500 psia. The partial pressure of the reactants is not particularly critical and depends predominantly on the amount and nature of the reactants employed and the desired result to be obtained. For instance, in non-aqueous hydroformylation processes, the carbon monoxide partial pressure is preferably from about 1 to about 120 psia and more preferably from about 3 to about 90 psia, while the hydrogen partial pressure is preferably about 10 to about 200 psia and more preferably from about 20 to about 160 psia. In general the $H_2$:CO molar ratio of gaseous hydrogen to carbon monoxide may range from about 1:10 to 100:1 or higher, the more preferred hydrogen to carbon monoxide molar ratio being from about 1:1 to about 10:1.

It is preferred to effect the hydroformylation reaction using a liquid phase in the reaction zone which contains one of the aforementioned rhodium complex catalysts and, as a solvent therefor, higher boiling liquid aldehyde condensation products. By the term "higher boiling liquid aldehyde condensation products", as used herein, is meant the complex mixture of high boiling liquid products which results from the condensation reactions of the aldehyde products of the hydroformylation process, as illustrated below in a series of equations involving the aldehyde, n-butyraldehyde, as a model. Such condensation products can be preformed or produced in situ in the hydroformylation process. The rhodium complex catalyst species is soluble in these relatively high boiling liquid aldehyde condensation products while exhibiting high catalyst life over extended periods of continuous hydroformylation.

Initially, the hydroformylation reaction can be effected in the absence or in the presence of small amounts of higher boiling liquid aldehyde condensation products as a solvent for the rhodium complex, or the reaction can be conducted with up to about 70 weight percent and even as much as about 90 weight percent, and more, of such condensation products, based on the weight of the liquid body in the hydroformylation reaction zone. Such "small amounts" of higher boiling liquid aldehyde condensation products can be as little as 5 weight percent, preferably more than 15 weight percent, based on the weight of the liquid body.

In the hydroformylation of, for example, propylene, two products are possible, namely normal and iso-butyraldehydes. Since normal - butyraldehyde is the more attractive product commercially, high normal/iso ratios of butyraldehydes are desirable. However, since the aldehydic products are themselves reactive, they slowly undergo condensation reactions, even in the absence of catalysts and at comparatively low temperatures, to form high boiling liquid condensation products. Some aldehyde product, therefore, is involved in various reactions as depicted below using n-butyraldehyde as an illustration:

The names inn parenthesis in the afore-illustrated equations, aldol I, substituted acrlein II, trimer III, trimer IV, dimer V, tetramer VI, and tetramer VII, are for convenience only. Aldodl I is formed by an aldol condensation; trimer III and tetramer VII are formed via Tischenko reactions; trimer IV by a transesterification reaction; dimer V and tetramer VI by a dismutation reaction. Principal condensation products are trimer III, trimer IV, and tetramer VII, with lesser amounts of the other products being present. Such condensation products, therefore, contain substantial quantities of hydroxylic compounds as witnessed, for example, by trimers III and IV and tetramer VII.

Similar condensation products are produced by self condensation of iso-butyraldehyde and a further range of compounds is formed by condensation of one molecule of normal-butyraldehyde with one molecule of iso-butyraldehyde. Since a molecule of normal-butyraldehyde can aldolize by reaction with a molecule of iso-butyraldehyde in two different ways to form two different aldols VIII and IX, a total of four possible aldols can be produced by condensation reactions of a normal/iso mixture of butyraldehydes.

Aldol I can undergo further condensation with iso-butyraldehyde to form a trimer isomeric with trimer III and aldols VIII and IX and the corresponding aldol X produced by self condensation of two molecules of iso-butyraldehyde can undergo further reactions with either normal or iso-butyraldehyde to form corresponding isomeric trimers. These trimers can react further analogously to trimer III so that a complex mixture of condensation products is formed.

It is highly desirable to maintain the substituted acrolein II and its isomers at low concentrations, e.g. below about 5 weight percent. The substituted acrolein II, specifically termed 2-ethyl-3-propylacrolein ("EPA"), is formed in situ along with other condensation products and has been-found to inhibit catalyst activity. The ultimate effect of EPA or like products is to reduce hydroformylation rates to such an extent that any process where the EPA is present in amounts greater than about 5 weight percent, even greater than about one percent by weight based on the weight of the liquid body, will suffer an economic penalty.

In certain instances, it may also be desirable to use minor amounts of an organic co-solvent which is normally liquid and inert during the hydroformylation process, e.g. polyalkylene oxide or toluene, particularly at start-up of the process. They can be allowed to be replaced in the liquid phase in the reaction zone by the higher boiling liquid aldehyde condensation products as the reaction proceeds.

The liquid body in the hydroformylation reaction zone will thus contain, in addition to the reactants and catalyst and any added diluent such as free ligand, aldehyde product and the aldols, trimers, diester, etc, derived from them (i.e., the higher boiling liquid aldehyde condensation products).

The hydroformylation reaction may be conducted in continuous, semi-continuous or batch fashion. If desired, the catalyst can be added to the hydroformylation reaction zone batchwise, continuously and/or incrementally. Various techniques may be employed to recover an aldehyde product, depending upon the particular manner in which the hydroformylation reaction system is operated. Two typical hydroformylation reaction systems are a gas recycle system and a liquid recycle system. The present invention is particularly well-suited for use in a hydroformylation reaction system which includes a liquid recycle. However, as discussed below, the present invention also may be used to advantage in a hydroformylation reaction system which employs a gas recycle. In addition, the present invention is useful in conjunction with hydroformylation reaction systems 10 which employ both a liquid recycle and a gas recycle.

In a liquid recycle system, a portion of the liquid body in the hydroformylation reaction zone is removed and processed for recovery of aldehyde product, after which the remaining liquid may be recycled to the hydroformylation reaction zone. For example, the liquid portion removed from the reaction zone may be passed through a let-down valve to substantially reduce the reaction pressure to, e.g., nearly atmospheric pressure. The resulting liquid may then be passed through a first vaporizer to flash off "lights" (e.g., hydrogen, carbon monoxide, unreacted olefin, etc.) at ambient temperature, and then introduced into a second vaporizer to "strip" or recover aldehyde product as an overhead fraction. The second vaporizer is typically maintained at an elevated temperature of about 100° C. or less to about 160° C. or higher, at a pressure of about 1mm. of Hg to about 1400 mm. of Hg. The operative conditions in the second vaporizer will depend primarily upon the nature of the aldehyde products being recovered.

The liquid fraction resulting from the removal of lights and aldehyde product from the withdrawn liquid hydroformylation reaction body, is referred to herein as the "stripped catalyst solution." This solution, which is normally recycled to the hydroformylation reaction zone, may be defined in terms of the amount of material removed or stripped, which may range from 10% to as high as 90% by weight of the portion of catalyst solution withdrawn from the hydroformylation reaction zone. Values lower than about 10% would be uneconomical because operation below this level would require high catalyst cycle rates. Values higher than about 90% are not practical because excessive concentration can lead to catalyst deactivation and/or high viscosities of the resulting stripped catalyst solution which would reduce the effectiveness of the scrubbing operation. It is most preferred to employ a solution from which 25 to 85% by weight of the material has been removed. The optimum amount of stripping for any given operation depends on several factors including the composition of the catalyst solution, the nature of the specific active catalyst species, the amount of material to be scrubbed with the stripped catalyst solution, and the temperature of the scrubbing operation.

The stripped catalyst solution typically comprises free triorganophosphorus ligand, unrecovered aldehyde product, some higher boiling liquid aldehyde condensation products and rhodium catalyst values. A major portion by weight of the stripped catalyst solution may comprise free triorganophosphorus ligand and aldehyde product.

The liquid recycle may be effected continuously or intermittently. At times, it may be desirable to bleed off a portion of the liquid recycle stream to, for example, regenerate deactivated rhodium catalyst, or to prevent an extraordinary build-up of the higher boiling liquid aldehyde condensation products or phosphine oxides, etc. It may also be desirable to add fresh or reactivated rhodium catalyst to the liquid recycle stream, or separately to the hydroformylation reaction zone. The temperature of the liquid recycle stream does not appear to be critical and may vary from about 20° C. to the maximum hydroformylation reaction temperature contemplated, and higher.

As described below in detail, in accordance with the present invention the stripped catalyst solution is employed to scrub gas streams in the system to recover olefin and aldehyde. For example, a vapor space above the liquid body in the hydroformylation reaction zone may be purged to control inerts and/or excess hydrogen. However, such purge streams also contain valuable components such as unreacted olefin and product aldehydes which, unless otherwise used or recovered, are lost from the system. These components may be recovered by scrubbing the gaseous purge stream with stripped catalyst solution.

In a gas recycle hydroformylation system, olefin together with hydrogen and carbon monoxide are passed through the liquid body in the hydroformylation reaction zone. An aldehyde product-containing vapor phase is continuously removed from the reaction zone, passed to a product separation zone where a liquid aldehyde-containing product is separated by condensation from the gaseous unreacted starting materials, and the gaseous unreacted starting materials are then recycled from the product separation zone to the reaction zone, preferably together with make-up starting materials. The rate at which these gases are recycled to the hydroformylation reaction zone is a rate which is at least as great as that required to maintain a mass balance in the reaction zone (see, e.g., the aforementioned U.S. Pat. No. 4,247,486).

In such a gas recycle system, the heat of reaction of the hydroformylation reaction may be removed and controlled by removing from the reaction zone a portion of the liquid body therein (i.e., "the catalyst solution"), passing that portion through a heat exchanger and then returning the resulting cooled portion to the reaction zone. As used herein, "cooled catalyst solution" refers to this removed and cooled portion of liquid catalyst solution. Typically, the cooled catalyst solution will have a temperature of about 5-20° C. cooler than the catalyst solution in the reaction zone. This cooled catalyst solution may be employed as a scrubbing solution in the process of the present invention in the same manner as the stripped catalyst solution in a liquid recycle process.

In some gas recycle hydroformylation processes, an additional portion of catalyst solution may be removed from the reaction zone and externally processed, for example, to reactivate the catalyst or to remove heavies. In the course of such external processing, before being returned to the reaction zone, the removed catalyst solution is generally stripped (to remove lights and aldehyde) and optionally cooled. Because one of the objects of external processing may be catalyst regeneration, the solution may be stripped so as to include essentially no aldehyde. Such stripped or cooled catalyst solutions may also be employed as a scrubbing solution in the process of the present invention.

In a hydroformylation system which..employs either a liquid or a gas recycle, or a combination of both, a stripped or cooled catalyst solution is used to recover unreacted olefin and aldehyde product, as well as other soluble (absorbable) components from gaseous vent streams or other gas streams existing in the hydroformylation system. The scrubbing can be effected using various types of conventional scrubbing equipment. For example, an effective scrubber is a countercurrent type contacting device such as a packed column. The absorbent (the stripped or cooled catalyst solution) enters the packed column at or near the top of the column, and flows downwardly to its base while the gaseous stream to be scrubbed enters the column near its bottom and flows upwardly. The portion of the gaseous stream that is not absorbed exits near the top of the column and the scrubbed catalyst solution, containing the dissolved (absorbed) gases, is removed from the bottom of the column.

A major advantage of the present invention is that no additional step is required to recover the absorbed gases from the catalyst solution absorbent, because that solution is returned directly to the hydroformylation reaction zone after the scrubbing operation, where the dissolved (absorbed) unreacted olefin may be subjected to reaction and the dissolved (absorbed) aldehyde product is subjected to the normal recovery steps.

For the scrubbing operation to be effective, it is necessary for the catalyst solution absorbent to have a lower concentration of those components to be absorbed from the gas stream than the concentration that it would have if it were in equilibrium with the gas stream at the temperature and pressure of the scrubber and at the composition of the gas stream. Since solubilities of olefins, aldehydes, and alcohols generally increase with lower temperatures, these compounds will be more effectively absorbed into a given stripped or cooled catalyst solution at lower temperatures. The lower limit for the temperature of the scrubbing operation is the temperature at which the stripped or cooled catalyst solution or portions of it starts to freeze. This lower temperature limit will vary with the particular stripped or cooled catalyst solution, but about 20° C is useful as a lower limit. The upper limit on scrubbing temperature is determined by both the effect of temperature on the ability of the stripped or cooled catalyst solution to absorb the gases and by the concern for deactivation of the catalyst An upper limit of about 175° C. is contemplated. The preferred range is 25° C. to 150° C.

The optimum temperature range for scrubbing depends on the specific stripped or cooled catalyst solution employed. For a solution that has been partially stripped of aldehyde and lights, a temperature from the mid to the upper end of the operable range is generally effective. For solutions that have not been stripped but only cooled, lower temperatures will be required.

The effectiveness of the scrubbing operation may be enhanced by optionally further cooling the particular stripped or cooled catalyst solution employed. Specifically, in the case of a liquid recycle system, for example, the stripped catalyst solution may be optionally cooled prior to contact with a gas stream in the scrubbing operation. The result of such cooling should be to bring the solution within the temperature ranges for scrubber operation given above. In the case of a gas recycle system, for example, the cooled catalyst solution may be optionally further cooled to a useful lower limit of 20° C.-35° C. to enhance the effectiveness of scrubbing. Further, the effectiveness of the scrubbing operation may also be controlled by adjusting the flow rate and pressure of the stripped or cooled catalyst solution during scrubbing.

The scrubbing operation will be most effective if the pressure is high. However, from a practical viewpoint, it is generally not economically justified to compress the gaseous vent streams to pressures greatly higher than the reactor pressure. Therefore, an upper pressure limit of 750 psia is suggested. The lower limit on pressure is determined by the pressure of the lowest pressure vent stream, which could be as low as 2 psia. The preferred scrubbing pressure range is 15 psia to 750 psia. In practice, the most preferred range depends on the particular circumstances, but generally it is preferred to operate the scrubber at or near the pressure of the gas stream being treated since this affords the most effective scrubbing without requiring any gas compression. However, in some situations, especially for low pressure vents, compression of the gas may be justified. To the extent that different gas streams may be it significantly different pressures, there may be an advantage to operating more than one scrubber, either in series or in parallel with regard to the flow of absorbent solution.

This invention is applicable to gas streams containing more than 1% olefin or more than $\frac{1}{2}$% aldehyde plus alcohol. Although it would have some utility at even lower concentrations of olefin, aldehyde or alcohol, it may not be economically justified. The invention will work with gas streams having compositions of up to 100% of olefin, aldehyde, or alcohol.

The appropriate ratio of gas stream flow rate to liquid absorbent solution flow rate will vary broadly depending on the compositions, temperatures, and pressures involved. The ratio to gas to liquid can be as low as 1 std L/hr of gas to 400 g/hr of liquid, or as high as 1 std L/hr of gas to 0.2 g/hr of liquid.

In liquid recycle systems, the olefin to be hydroformylated may have 2 to 30 carbon atoms, preferably 3 to 14 carbon atoms. Illustrative olefins are alpha-olefins, internal olefins, alkyl alkenoates, alkenyl alkanoates, alkenyl alkyl ethers, alkenols, and the like; e.g., ethylene, propylene, 1-butene, 1-hexene, 1-octene, 1-nonene, 1-decene, 1-undecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-pentene, 2-hexene, 2-heptene, propylene dimers, propylene trimers, propylene tetramers, 2-ethyl hexene, 2-octene, styrene, 3-phenyl-1-propene, 1,4-hexadiene, 1,7-octadiene, 3-cyclohexyl-1-butene, allyl butyrate, methyl methacrylate, vinyl ethyl ether, vinyl methyl ether, allyl ethyl ether, n-propyl-7-octenoate, 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenyl-benzene, eugenol, iso-eugenol, safrole, iso-safrole, anethol, 4-allylanisole, indene, limonene, beta-pinene, dicyclopentadiene, cyclooctadiene, camphene, linalool, and the like.

In a gas-recycle hydroformylation process, it is preferred to use alpha-olefins of 2 to 5 carbon atoms, preferably 2, 3 or 4 carbon atoms. Such alpha-olefins are characterized by a terminal ethylenic carbon-to-carbon bond which may be a vinylidene group, i.e., $CH_2=C-$, or a vinyl group, i.e., $CH_2=CH-$. They may be straight-chain or branched-chain and may contain groups or substituents which do not essentially interfere with the course of this process. Illustrative alpha-olefins include ethylene, propylene, 1-butene, iso-butylene, 2-methyl-1-butene, 1-pentene, and the like. The most preferred alpha-olefin for a gas recycle system is propylene.

Figure 1A:
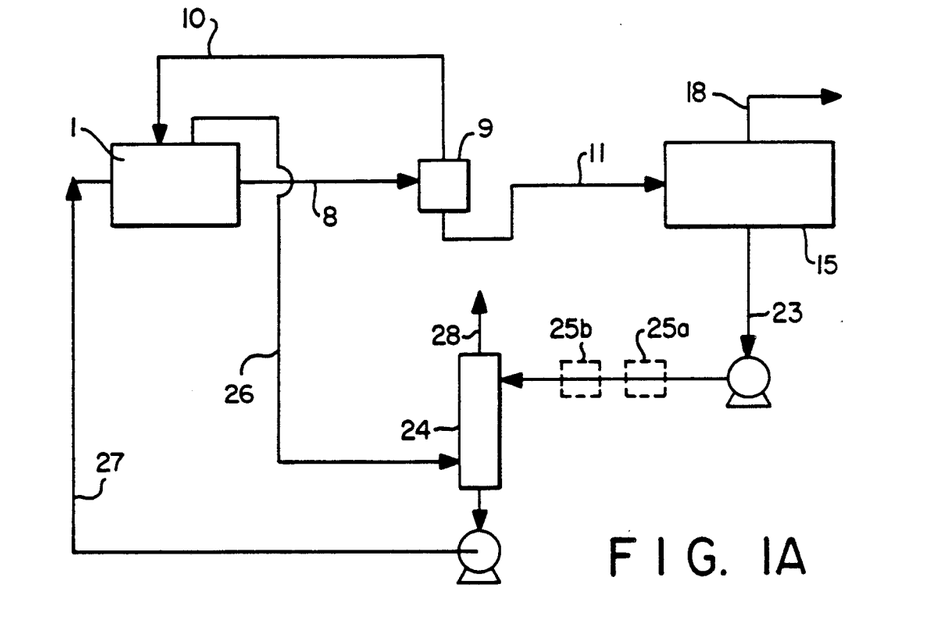

The invention may be further illustrated with reference to the accompanying drawings, in which FIG. 1A schematically shows the process of the present invention in a liquid recycle process.

Referring to FIG. IA a portion of the liquid hydroformylation reaction mixture is removed from the reactor 1 via line 8 to a separator 9 where entrained gas bubbles are separated from the liquid and returned to the vapor space of the reactor via line 10. The resulting liquid is passed from separator 9 via line 11 to a product separation means 15 where most of the aldehyde and essentially all of the $C_3S$ (i.e., propylene and propane) are separated from the heavier liquid catalyst solution. The crude aldehyde product of line 18 may be treated by conventional distillation to separate various aldehyde and condensation products. The stripped catalyst solution exits the separator via line 23 to scrubber 24. Optionally, a thin film evaporator 25a may be employed to remove heavier condensation products from the stripped catalyst solution if required. Also a cooler 25b may be employed if necessary.

Gaseous purges are taken from reactor 1 by line 26 to scrubber 24 where $C_3s$ and aldehyde are absorbed by the stripped (and optionally cooled) catalyst solution and the resulting liquid catalyst solution, containing absorbed aldehyde and $C_3S$, is returned directly to reactor 1 via line 27. Excess hydrogen and inerts are purged from the scrubber via line 28. The single reactor 1 can of course be replaced by a plurality of reactors in series or parallel. Although not necessarily shown, it can appreciated by one of ordinary skill in the art that at least some propane is allowed to escape from the system.

Figure 1B:
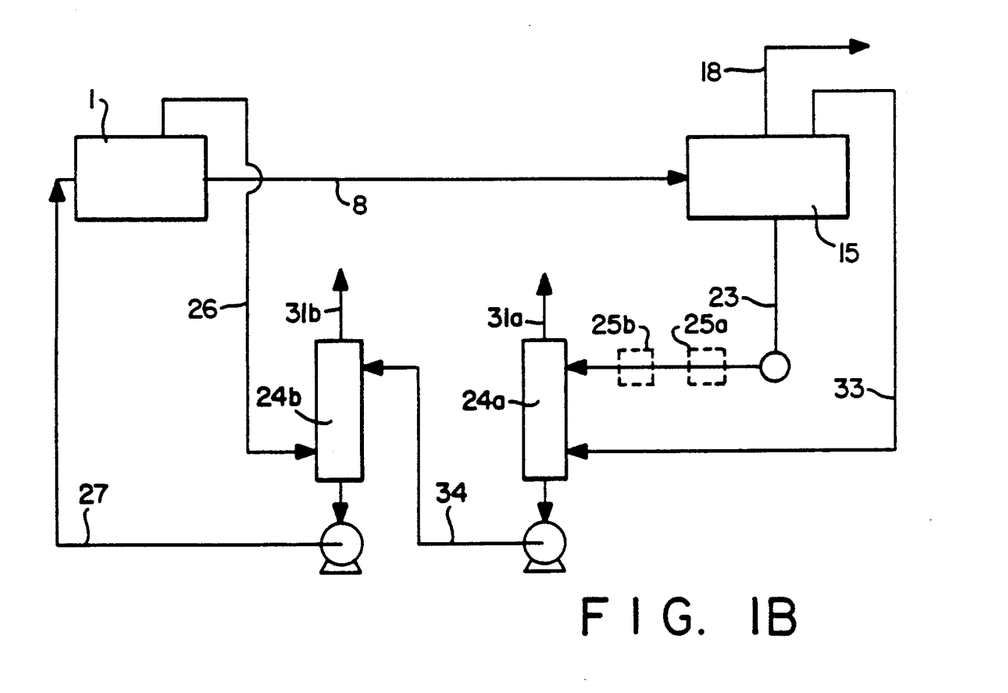
FIG. 1B illustrates a further embodiment in which multiple scrubbers are employed.

In another embodiment of the present invention, with reference to FIG. IB, a portion of the liquid hydroformylation reaction mixture is removed from the reactor 1 via line 8 to a product separation means 15 where most of the aldehyde and essentially all of the $C_3S$ are separated from the heavier liquid catalyst solution. The crude aldehyde product of line 18 may be treated by conventional distillation to separate various aldehyde .and condensation products. The stripped catalyst solution exits the separator via line 23 to scrubber 24a. Optionally, a thin-film evaporator 25a may be employed to remove heavier condensation products from the stripped catalyst solution if required. Also a cooler 25b may be employed if necessary. The stripped $C_3s$ and other dissolved gases removed from the liquid catalyst solution in separator 15 and not contained in the crude aldehyde stream 18 are taken from separator 15 to scrubber 24a via line 33 where $C_3s$ and aldehyde are absorbed by the stripped (and optionally cooled) catalyst solution. Excess hydrogen and inerts are purged from scrubber 24a via line 31a.

Catalyst solution from scrubber 24a, now containing absorbed $C_3s$ and aldehyde, is taken to scrubber 24b via line 34. Gaseous purges are taken from reactor 1 by line 26 to scrubber 24b where additional $C_3s$ and aldehyde are absorbed by the catalyst solution. The resulting liquid catalyst solution, containing absorbed aldehyde and $C_3s$, is returned to reactor 1 via line 27. Excess hydrogen and inerts are purged from the scrubber 24b via line 31b. It is desirable to operate scrubber 24b at a higher pressure than that of scrubber 24a. For example, scrubber 24b can be operated at a pressure dictated by the pressure of line 26 whereas the pressure of scrubber 24a can be operated at a pressure dictated by the pressure of line 33. The single reactor 1 can of course be replaced by a plurality of reactors in series or parallel.

In order to more fully describe the subject invention but without limiting same, the following examples are provided.

EXAMPLE 1

A continuous 53-day test run was made in a bench-scale propylene hydroformylation unit employing a liquid recycle and a rhodium/TPP catalyst system. A packed scrubber was employed to recover olefin, aldehyde and other soluble gaseous components from the reactor vent stream.

The hydroformylation reactor was operated under typical conditions of reactor temperature, reactor pressure, CO partial pressure, $H_2$ partial pressure, $C_3H_6$ partial pressure, Rh concentration, TPP concentration, vaporizer temperature, and vaporizer pressure to yield a total average reaction rate of 2.3 gmoles/L/hr and a Catalyst Activity value of 72%* at Day 30, and 51% at Day 53. (* Activity as a percent of the initial activity.)

The liquid leaving the reactor contained a large amount of gas and therefore a gas-liquid separator was used to allow the entrained gas bubbles to separate from the liquid. This gas was permitted to flow back to the vapor space of the reactor while the remaining liquid was directed to a vaporizer to initiate product separation and recovery phases of the process. The primary purpose of the vaporizer is, of course, to separate aldehyde from the heavier catalyst solution. It also necessary to remove heavies at the same rate at which they are being formed. Therefore, to accommodate both purposes, the vaporizer was operated at a temperature of about 130° C. and at a pressure of 2.5 psia.

The now partially stripped catalyst solution was cooled to 60° C. and was used to scrub olefin, aldehyde and other soluble gaseous components from the reactor vent stream. Over the course of the 53-day run the stripped catalyst solution was characterized by aldehyde levels which ranged from 25–35% of that present in the unstripped solution. The 53-day average level was about 30% . The scrubbing was effected in a conventional countercurrent-type contacting device. Accordingly, a packed column was used with the stripped catalyst solution entering the top of the column and flowing downwardly while the gas entered near the bottom and flowed upwardly. The resulting catalyst solution now containing dissolved gases was returned directly to the reactor.

For maximum scrubbing efficiency the pressure of the scrubber should be normally as high as possible, determined by the pressure of the gas in the stream to be scrubbed. In this case, the scrubber was operated at 245 psia and 60° C., utilizing the stripped catalyst solution from the product separation step. The stripped solution. was also cooled from 130° C. to 60° C. by passing the solution through an uninsulated feed line. The composition of the stripped catalyst solution fed to the scrubber was:

| | |
|---|---|
| Propylene + Propane | <0.5 wt. % |
| Total Butyraldehyde | 8-16 wt. % |
| Butyraldehyde Dimers | 2-5 wt. % |
| Butyraldehyde Trimers + "Heavies" | 55-75 wt % |
| Triphenylphosphine + Oxide | 12-16 wt. % |

The propylene in the reactor vent was 0.104 gmole/hr or 23.5 mole %, and the total butyraldehyde was 0.0306 gmole/hr or 6.9 mole %. Without the scrubber, this valuable raw material and product would have been vented from the system and lost. However, in this example, this vent stream was passed through the scrubber and 97.8% of the propylene and 92.5% of the butyraldehyde were recovered. The use of the scrubber had no effect on the rate of catalyst deactivation.

The specific scrubbing conditions and results were as follows:

| Scrubbing Conditions and Results | |
|---|---|
| Liquid Flow Rate | 7.6 gmole/hr |
| Gas inlet Flow Rate | 9.9 std. L/hr |
| Length/Diameter of Scrubber | 18 inches/1.05 moles |
| Packing | ¼" glass rings |
| Propylene in Inlet Gas Stream | 0.104 gmole/hr |
| Propylene in Outlet Gas Stream | 0.0023 gmole/hr |
| Aldehyde in Inlet Gas Stream | 0.0306 gmole/hr |
| Aldehyde in Outlet Gas Stream | 0.0023 gmole/hr |
| Propylene Recovery | 97.8% |
| Aldehyde Recovery | 92.5% |

EXAMPLE 2

In another test facility, a packed scrubber was tested in a similar fashion as in Example 1. Again, a normal catalyst activity decline rate was observed. The operation of the scrubber had no detectable detrimental effect on the catalyst in any way.

| Scrubbing Conditions and Results | |
|---|---|
| Liquid Flow Rate | 4.2 gmole/L/hr |
| Gas Inlet Flow Rate | 9.9 std L/hr |
| Length/Diameter of Scrubber | 18 inches/1.05 inches |
| Packing | ¼" glass rings |
| Propylene in Inlet Gas Stream | .0843 gmole/hr |
| Propylene in Outlet Gas Stream | .0029 gmole/hr |
| Aldehyde in Inlet Gas Stream | .0286 gmole/hr |
| Aldehyde in Outlet Gas Stream | .0035 gmole/hr |
| Propylene Recovery | 96.6% |
| Aldehyde Recovery | 87.8% |

What is claimed is:

1. A process for the recovery of absorbable components from a gaseous stream of a process for the production of aldehyde by the rhodium-catalyzed hydroformylation of olefins containing 2 to about 30 carbon atoms comprising:
   contacting a gaseous stream containing an absorbable component selected from the group consisting of unreacted olefin and product aldehyde with a rhodium catalyst solution selected from the group consisting of a stripped catalyst solution, a cooled catalyst solution and a stripped and cooled catalyst solution at a temperature of about 20° C. to about 175° C. and at a pressure of about 2 psia to about 750° C. psia sufficient to absorb at least a portion of the absorbable component into the catalyst solution to form an absorbed component catalyst solution and reintroducing the absorbed component catalyst solution without desorption to a hydroformylation reaction medium.

2. The process according to claim 1 wherein the temperature is about 25° C. to about 150° C.

3. The process according to claim 1 wherein the pressure is about 15 psia to about 750° psia.

4. The process according to claim 1 wherein the olefin is propylene and the catalytically absorbable component is selected from the group consisting of propylene and butyraldehyde.

5. The process according to claim 1 wherein the gaseous stream is an internal gaseous stream.

6. The process according to claim 1 wherein the gaseous stream is a vent stream.

7. The process according to claim 1 wherein said gaseous stream is a vent stream and said hydroformylation process is an liquid recycle process.

8. The process according to claim 1 wherein said gaseous stream is a vent stream and said hydroformylation process is an gas recycle process.

9. In a process of the production of aldehyde by the rhodium-catalyzed hydroformylation of olefins containing 2 to about 30 carbon atoms which comprises contacting an olefin with carbon monoxide and hydrogen in a liquid body in a hydroformylation reaction zone in the presence of a rhodium complex catalyst consisting essentially of rhodium in complex combination with carbon monoxide and an organophosphorus ligand, and in the presence of solvent and free organophosphorus ligand, removing a portion of the liquid body from said reaction zone, recovering product aldehyde from said withdrawn portion, and recycling the resulting stripped liquid to the hydroformylation reaction zone, the improvement which comprises recovering an absorbable component selected from the group consisting of unreacted olefin and product aldehyde from a gaseous stream of the process by contacting said gaseous stream with said stripped liquid at a temperature of about 20° C. to about 175° C. and at a pressure of about 2 psia to about 750 psia sufficient to absorb at least a portion of said absorbable component into said stripped liquid to form an absorbed component liquid, and reintroducing said absorbed component liquid without desorption to the hydroformylation reaction zone.

10. The process according to claim 9 wherein the stripped liquid is cooled prior to contact with said gaseous stream.

11. The process according to claim 9 wherein the temperature is about 25° C. to about 150° C.

12. The process according to claim 9 wherein the pressure is about 15 psia to about 750 psia.

13. The process according to claim 9 wherein the olefin is propylene and the absorbable component is selected from the group consisting of propylene and butyraldehyde.

14. In a process for the production of aldehyde products by the rhodium-catalyzed hydroformylation of alpha-olefins containing 2 to 5 carbon atoms which comprises contacting said alpha-olefin with hydrogen and carbon monoxide in a liquid body in a hydroformylation reaction zone, in the presence of a rhodium in complex combination with carbon monoxide and an organophosphorus ligand, removing a vapor from the reaction zone, which vapor contains aldehyde product and unreacted gaseous starting materials, recovering aldehyde product from said vapor and recycling gaseous unreacted starting materials to the hydroformylation reaction zone, wherein a portion of the liquid body in the reaction zone is removed therefrom and cooled and the resulting cooled liquid is returned to the reaction zone, the improvement comprising recovering an absorbable component selected from the group consisting of unreacted olefin and product aldehyde from a gaseous stream of the process by contacting said gaseous stream with said cooled liquid at a temperature of about 20° C. t about 175° C. and at a pressure of about 2 psia to about 750 psia sufficient to absorb at least a portion of said absorbable component into said cooled liquid to form an absorbed component liquid, and reintroducing said absorbed component liquid without desorption to said hydroformylation reaction zone.

15. The process according to claim 14 wherein the temperature is about 20° C. to about 150° C.

16. The process according to claim 14 wherein the pressure is about 15 psia to about 750 psia.

17. The process according to claim 14 wherein the olefin is propylene and the absorbable component is selected from the group consisting of propylene and butyraldehyde.

* * * * *